US006548725B2

(12) United States Patent
Froment et al.

(10) Patent No.: US 6,548,725 B2
(45) Date of Patent: Apr. 15, 2003

(54) PROCESS FOR MANUFACTURING OLEFINS

(75) Inventors: Gilbert Fernand Alphonse Froment, Deurle-St. Martens Latem (BE); Wilfried Jozef Hippolyte Dehertog, Tervuren (BE); Mark P. Kaminsky, Winfield, IL (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/918,925

(22) Filed: Jul. 31, 2001

(65) Prior Publication Data

US 2001/0056217 A1 Dec. 27, 2001

Related U.S. Application Data

(63) Continuation of application No. 09/405,582, filed on Sep. 27, 1999, now abandoned, which is a continuation-in-part of application No. 09/161,845, filed on Sep. 28, 1998, now abandoned.

(51) Int. Cl.[7] .............................. C07C 4/06; C07C 2/00
(52) U.S. Cl. ...................... 585/653; 585/650; 585/651; 585/407; 585/418
(58) Field of Search ................................ 585/650, 651, 585/653, 407, 418

(56) References Cited

U.S. PATENT DOCUMENTS

| | | | | | |
|---|---|---|---|---|---|
| 3,972,832 A | * | 8/1976 | Butter et al. | ................... | 502/77 |
| 4,112,056 A | * | 9/1978 | Chen et al. | .................. | 423/704 |
| 4,356,338 A | * | 10/1982 | Young | .......................... | 585/407 |
| 4,394,300 A | | 7/1983 | Chu et al. | .................... | 252/455 |
| 4,599,477 A | | 7/1986 | Robinson et al. | ........... | 585/622 |
| 4,801,567 A | | 1/1989 | Moorehead | .................. | 502/77 |
| 4,861,930 A | | 8/1989 | Cottrell et al. | .............. | 585/317 |
| 5,166,455 A | | 11/1992 | Chin et al. | ................... | 568/697 |
| 5,389,232 A | | 2/1995 | Adewuji et al. | ............. | 208/120 |
| 5,574,199 A | * | 11/1996 | Beck et al. | .................. | 585/407 |

* cited by examiner

Primary Examiner—Thuan D. Dang
(74) Attorney, Agent, or Firm—James R. Henes (57) ABSTRACT

A catalyst and an improved process for producing olefins by catalytic naphtha cracking are described. The process provides relatively higher yields over a commercially important range of naphtha conversion, while providing about the same or lower yields of aromatics and methane over the range. In the process, a hydrocarbon naphtha feedstock including a hydrocarbon having about three to about twenty carbon atoms per molecule is passed into a reactor containing a pentasil zeolite catalyst. The catalyst includes about 0.1 to about 10 weight percent phosphorus and about 0.1 to about 10 weight percent of a promoter metal selected from the group consisting of gallium, germanium, tin and mixtures thereof. The hydrocarbon may be passed into the reactor together with a diluent selected from the group consisting of steam, nitrogen, methane, and ethane and mixtures thereof. Alternatively, the hydrocarbon may be passed into the reactor together with additional propane.

8 Claims, 8 Drawing Sheets

PROCESS FOR MANUFACTURING OLEFINS

This application is continuation of U.S. patent application Ser. No. 09/405,582, by Froment et al., filed Sep. 27, 1999, now abandoned, which application is a continuation-in-part of U.S. patent application Ser. No. 09/161,845, by Froment et al., filed Sep. 28, 1998, now abandoned, and claims the benefit of the referenced applications which are specifically incorporated herein, in their entirety.

BACKGROUND OF THE INVENTION

I. Field of the Invention

The present invention relates to an improved process for catalytically cracking a naphtha hydrocarbon feed to produce light olefins products, such as ethylene. propylene and butylene, and a relatively less aromatics. The process includes contacting a naphtha hydrocarbon feed with a pentasil zeolite catalyst which contains phosphorus and a promoter metal. The present invention also relates to a catalyst composition useful for manufacturing light olefins from a naphtha hydrocarbon feed.

II. Description of the Prior Art

Production of light olefins, such as ethylene and propylene, is a major industrial process and forms a backbone of the chemical industry. Conventionally, naphtha feedstocks containing paraffinic and isoparaffinic compounds, naphthenes and aromatics are thermally cracked to produce light olefins. The naphtha thermal cracking process of choice has traditionally been steam pyrolysis, usually performed by exposing naphtha and steam to relatively high temperatures in the tubular coils of a fired heater.

Examples of previously known olefin processes include those described in U.S. Pat. Nos. 5,446,229 and 5,254,781. Although steam pyrolysis is widely practiced, this process is energy intensive, not very selective, produces coke and releases significant amounts of carbon dioxide into the air. Accordingly, chemical manufacturers have long recognized a need for an alternative naphtha cracking process.

One alternative to steam pyrolysis process is a naphtha catalytic cracking process, in which a hydrocarbon feed is contacted with a catalyst and the hydrocarbon is converted selectively to an olefin-containing mixture. Although various naphtha catalytic cracking processes have been previously proposed, none has been adopted by the chemical manufacturing industry on a commercial scale. Apparently, previous naphtha catalytic cracking processes do not produce commercially important light olefins with sufficient selectivity or yield, and typically produce undesirable amounts of methane and aromatics as unwanted byproducts. In contrast, a practical and economic naphtha catalytic cracking process will selectively produce ethylene and propylene in abundance, while producing minimal amounts of methane and aromatics.

The process of the present invention employs a pentasil zeolite catalyst system which includes phosphorus together with certain promoter metals. Although pentasil zeolite materials, such as zeolite ZSM-5, have been widely publicized as hydrocarbon conversion catalysts, the present invention is directed to specific uses of a pentasil zeolite catalyst system for selectively cracking naphtha to produce light olefins. Examples of previous catalyst systems include U.S. Pat. No. 3,972,832; U.S. Pat. No. 4,044,065; and U.S. Pat. No. 5,171,921.

One aspect of the present invention is to convert a hydrocarbon stream such as, for example, a naphtha stream, to a stream including light olefins, such as ethylene and propylene. Another aspect of the invention is to convert a light hydrocarbon stream including $C_5$ to $C_7$ paraffins and isoparaffins to an olefin stream which includes ethylene and propylene. Still another aspect of this invention is to convert a hydrocarbon stream to olefins, without coproducing a significant amount of methane and aromatics. Other aspects of the invention may be present in the further description and examples.

SUMMARY OF THE INVENTION

The invention is a naphtha cracking catalyst and an improved catalytic naphtha cracking process for producing olefins from paraffins, particularly paraffins which are present in a hydrocarbon mixture commonly known as naphtha. The process provides relatively higher propylene yields and significantly lower methane yields over the commercially important range of about 60 to about 90 percent naphtha conversion, while providing about the same or lower yields of aromatics and light paraffins over the range, as compared to well known prior art catalytic and thermal processes. Additionally, the process resists deactivation of the catalyst by coking.

In one aspect, the invention is a process for producing a relatively light olefin. Naphtha is the preferred feedstock for this process. In the process, a hydrocarbon feedstock, which includes hydrocarbons having about three to about twenty carbon atoms, preferably a paraffinic and isoparaffinic hydrocarbons having about four to about eleven carbon atoms per molecule, is passed into a reactor containing a pentasil zeolite catalyst. The zeolite-containing catalyst typically includes about 0.1 to about 10 weight percent phosphorus and about 0.1 to about 10 weight percent of a promoter metal selected from the group consisting of gallium, germanium, tin and mixtures thereof. At least a portion of the hydrocarbon is converted to produce an olefin having about two to about three carbon atoms per molecule. The hydrocarbon may be passed into the reactor together with a heat-conducting diluent such as steam, nitrogen, alkanes such as methane and ethane, and mixtures thereof which are substantially inert under the process conditions used.

In another aspect, the invention is a process for producing an olefin, which process comprises contacting a naphtha which includes a paraffin having about four to about eleven carbon atoms per molecule with a catalyst in a reactor at a temperature of about 400 to about 650 degrees C. and a pressure of about one to about three atmospheres. The catalyst is a pentasil zeolite catalyst having a silicon to aluminum atomic ratio of about 10 to about 400 and On which is typically placed about 0.1 to about 10 weight percent phosphorus and about 0.1 to about 10 weight percent of a promoting metal selected from the group consisting of germanium, gallium, tin, and mixtures thereof. At least a portion of the naphtha is cracked in the reactor to produce olefins having about two to about three carbon atoms per molecule. The naphtha may be passed into the reactor together with a diluent in the molar ratio in the range of about 9 to about 0.1. Alternatively, the naphtha may be passed into the reactor together with additional propane in a molar ration in the range of about 6 to about 1. A portion of the reactor product may be recycled to the reactor.

In yet another aspect, the invention is a catalyst useful for producing light olefins from a hydrocarbon mixture, such as a naphtha, which includes one of more paraffins. The catalyst comprises a pentasil zeolite comprising silicon and aluminum in a silicon to aluminum atomic ratio of about 10 to about 400, about 0.1 to about 10 weight percent phosphorus, and about 0.1 to about 10 weight percent of a promoting metal selected from the group consisting of germanium, gallium, tin and mixtures thereof. Preferably, the pentasil zeolite is ZSM-5, and the weight ratio of phosphorus to promoter metal is in the range of about 1:1 to about 5:1.

DETAILED DESCRIPTION OF PREFERRED ASPECTS OF THE INVENTION

In a preferred aspect, the present invention is a process in which a hydrocarbon feedstock comprising paraffins, aromatics, naphthenes, or mixtures thereof, is at least partially catalytically cracked to produce valuable lower olefins such as, for example, ethylene, propylene and butylene. The process includes contacting the hydrocarbon feedstock at effective reaction conditions with a pentasil zeolite catalyst which includes phosphorus and a promoter metal selected from the group consisting of gallium, germanium, tin and mixtures thereof.

Generally, naphthas comprise the most suitable feedstock materials. Naphtha means a volatile hydrocarbon mixture which is liquid at room temperature and pressure. Preferred naphthas comprise one or more paraffins, each of the paraffins having about three to about twenty carbon atoms per molecule, more preferably about four to about eleven carbon atoms per molecule, and exhibit an atmospheric volumetric average boiling point in the range of about negative 22 to about 466 degrees C., more preferably about negative 1 to 204 degrees C. For the present purposes, paraffin means a saturated hydrocarbon of the empirical chemical formula $C_nH_{2n+2}$ wherein n is an integer greater than zero. Paraffins include normal paraffins, which are unbranched, and isoparaffins, which contain at least one branched carbon chain per molecule. Especially preferred naphthas comprise proportions of various hydrocarbons present in the following ranges, expressed in weight percent of the total naphtha weight:

| Normal Paraffins | Isoparaffins | Naphthenes | Olefins | Aromatics |
|---|---|---|---|---|
| 6–34% | 20–78% | 1–35% | 0–1.0% | 0–18% |

In practicing this aspect of the invention, contacting of the hydrocarbon feedstock and the pentasil zeolite catalyst is carried out at conditions which favor the formation of lower olefins. Preferably, the hydrocarbon feedstock and the pentasil zeolite catalyst, which is described in more detail below, are contacted in a reactor. For the present purposes, reactor means an apparatus such as, for example, a vessel, a tube, a riser or a coil, which encloses a volume which is maintained at reaction conditions effective to promote a desired chemical reaction. The invention may be practiced utilizing any of various types of reactors, some of which are known in the art as, for example, a fixed bed down flow reactor with feed preheating, a radial flow reactor, a fluidized bed reactor, or a transport riser reactor.

The process of the instant invention is highly endothermic. Preferably, fluidized bed solid catalyst conversion procedures are used in which the feed hydrocarbon material is contacted in vapor form with fluidized catalyst particles comprising pentasil zeolite catalyst. On the other hand, this aspect of the invention can be successfully practiced using fixed bed procedures. When a fixed bed of catalyst is employed, the use of reactors in series with interstage heating is advantageous.

Moving catalyst bed technology, such the catalyst regenerating technology employed commercially for the reforming of naphtha fractions, may be advantageously employed with the instant invention. A preferred reactor system is a moving bed radial flow multi-stage reactor with interstage heating, as described in U.S. Pat. Nos. 3,652,231; 4,094,814; 4,110,081; and 4,403,909, which are hereby incorporated by reference in their entirety, and specifically for their teachings regarding moving catalyst bed technology and regeneration systems. This reactor system normally employs a spherical catalyst having a diameter of about 0.03 to about 0.13 of an inch (about 0.76 to about 3.3 millimeter).

For the present purposes, effective reaction conditions means conditions which favor the formation of lower olefins. Conditions which favor the formation of lower olefins and, therefore, should be maintained in the reactor include a temperature of out 400 to about 650 degrees C., preferably about 480 to about 635 degrees C., more preferably about 540 to about 620 degrees C., and most preferably about 540 to about 600 degrees C. Preferably, the total pressure in the reactor of this preferred aspect of the invention typically about 1 to about 2 atmospheres absolute, more preferably about 1 to about 1.5 atmospheres absolute, most preferably about 1 to about 1.15 atmospheres absolute.

The partial pressure attributable to all hydrocarbons present in the reactor at effective reaction conditions is about 0.1 to about 0.9 atmospheres absolute. The hydrocarbon feedstock may be admixed with a diluent useful for heat transfer composed of nitrogen, steam or a relatively refractory hydrocarbon such as, for example, methane or ethane. The partial pressure of the diluent at effective reaction conditions may be from about 0.9 to about 0.1 atmospheres absolute.

The hydrocarbon feedstock may be admixed with a co-feed composed substantially of propane. In this case, the hydrocarbon feedstock and the co-feed are passed into the reactor together, and the molar ratio of propane passed into the reactor to the hydrocarbon passed into the reactor is preferably about 6 to about 1. Some portion of reactor products may be recycled back to the reactor.

Preferably, space time in the reactor is about 1 to about 180 grams of catalyst per mole of hydrocarbon feedstock per hour, more preferably about 50 to about 100 grams of catalyst per mole of hydrocarbon feedstock per hour. For the present purposes, space time means the mass of catalyst in grams present in the reactor for each mole per hour of hydrocarbon feedstock which enters the reactor.

In another preferred aspect, the invention is a catalyst. The active catalyst component is a phosphorus-containing pentasil zeolite such as, for example, ZSM-5 zeolite or ZSM-11 zeolite. For the present purposes, zeolite means a crystalline molecular sieve, which has an open porous structure and an ion exchange capacity. A zeolite may contain elements in addition to silicon and aluminum in their framework structures. For example, a zeolite may be a silicate having a framework structure into which a relatively small quantity of another element has been substituted, such as aluminum in ZSM-5 aluminosilicalite or boron in HAMS-1-B borosilicate.

Silicalite is described in U.S. Pat. No. 4,061,724, which is hereby incorporated by reference in its entirety, and especially for its teachings regarding silicalite. HAMS-1-B is described in U.S. Pat. No. 4,269,813, which is hereby incorporated by reference in its entirety, and especially for its teachings regarding HAMS-1-B.

Pentasil means a family of zeolites having similar framework structures with ZSM-5 and ZSM-11 as its two end members. The framework structures are formed by linking chains of 5-membered ring secondary building units. Further information regarding pentasil zeolites may be found at pages 12–14 of *Shape Selective Catalysis in Industrial Applications* by N.Y. Chen et al., copyright 1989, published by Marcel Dekker, Inc. of New York.

The pentasil zeolite useful in this invention also includes a promoter metal selected from the group consisting of gallium, germanium, tin, and mixtures thereof. Preferably, the zeolite is a phosphorus-containing ZSM-5 having a surface silicon to aluminum atomic ratio in the range of about 10 to about 400, preferably about 30 to about 180, and more preferably about 30 to about 60.

The silicon to aluminum atomic ratio of the zeolite is conveniently controlled by regulating the amounts of components which are used to formulate the zeolite in accordance with known procedures. For example, phosphorus may be added to the formed pentasil zeolite by impregnating the zeolite with a phosphorus compound in accordance with the procedures described, for example, in U.S. Pat. No. 3,972,832 and U.S. Pat. No. 5,171,921 (which patents are incorporated herein by reference in their entirety, and especially for their teachings regarding pentasil zeolite). Alternatively, the phosphorus compound can be added to a multicomponent mixture from which the pentasil catalyst is formed. In either case, the phosphorus compound is added in an amount sufficient to provide a final pentasil zeolite composition having preferably about 0.1 to about 10 weight percent phosphorus, more preferably about 0.5 to about 2 weight percent phosphorus, most preferably about 0.75 to about 1.5 weight percent phosphorus, and usually about 1 weight percent phosphorus, based on the total weight of the pentasil zeolite.

The promoter metal may be incorporated into the phosphorus-containing pentasil zeolite (hereinafter referred to as "P-pentasil zeolite") by any suitable manner known in the art which results in a relatively uniform dispersion of the second metal such as, for example, by ion exchange, cogelation, or impregnation. The promoter is added in an amount sufficient to provide a final P-pentasil zeolite having preferably about 0.1 to about 10 weight percent of the promoter metal, more preferably about 0.5 to about 5 weight percent of the promoter metal, most preferably about 0.75 to about weight percent of the promoter metal, and ideally about 1 weight percent of the promoter metal based on the total weight of the pentasil zeolite.

The phosphorus-containing pentasil zeolite described in this invention is preferably combined with or incorporated into known inert binders or matrices such as alumina, silica and silica alumina and may be formed into pellets, spheres or other discrete forms suitable for use in a hydrocarbon conversion reactor. In a typical procedure, a pentasil zeolite product may be formed into discrete forms by extruding from a die and chopping. Typical extrudates may be about 1 to about 10 millimeters in diameter, often about 2 to about 6 millimeters in diameter, and about 4 to about 20 millimeters in length as suitable for the reactor system utilized. Alternatively, a zeolite binder product may be formed into a sphere by rolling or by dropping in a liquid filled tower. Typical spheres are about 0.03 to about 0.5 inches (about 0.75 to about 12 millimeters) in diameter.

For use in this invention, a pentasil zeolite is modified by incorporation of phosphorus and a promoter metal species. Typically, phosphorus is incorporated by adding a suitable phosphorus containing compound to the zeolite-containing material in a liquid medium, followed by drying and calcining. Similarly, the promoter metal may be incorporated by methods including impregnation and ion exchange, either to the zeolite alone or to the zeolite incorporated into the binder. Alternatively, it is contemplated that one or more of the promoter metals may be added to the binder or to the zeolite-binder product.

The binder or matrix generally comprises about 5 to about 90 weight percent of the catalyst composition, preferably about 20 to about weight percent, and more preferably about 30 to about 50 weight percent. The phosphorus-containing pentasil zeolite need not be treated with steam after incorporation of phosphorus.

For the present purposes, naphtha conversion means a mole-weighted average of the individual conversions of fifteen non-aromatic key components which are present in the naphtha but are not created under reaction conditions. The use of the key components in calculating naphtha conversion tends to minimise ambiguities which might otherwise arise when individual components are simultaneously created and destroyed in the same reactor. More information regarding the determination of naphtha conversion may be found in a technical paper entitled "Scaling Up of Naphtha Cracking Coils" by P. S. Van Damme, G. F. Froment, and W. S. Balthasar which appears in Industrial Engineering Chemistry Process Design and Development, 1981, vol. 20, at page 366, which is incorporated by reference herein.

The following Examples are presented order to better communicate, but not limit the invention.

EXAMPLE 1

Conversion of Naphtha Over 1 Weight Percent P on HZSM-5 Zeolite of Silicon to Aluminum Atomic Ratio 30

As a control procedure, conversion of a light naphtha was demonstrated in the presence of a previously known pentasil zeolite, 1 weight percent phosphorus on HZSM-5 zeolite of silicon to aluminum ratio equal to 30. The most important components of a typical naphtha feed, employed in this Example 1, are shown below in Table 2.

TABLE 2

Naphtha Feed Composition (weight percent)

| hydrogen | 0.00 | 2,2-dimethylbutane | 2.83 |
|---|---|---|---|
| methane | 0.00 | 2,3-dimethylbutane | 3.50 |
| ethylene (C2H4) | 0.00 | cyclohexane | 0.52 |
| ethane | 0.00 | 2,2-dimethylpentane | 1.38 |
| propylene (C3H6) | 0.00 | 2,4-dimethylpentane | 1.65 |
| propane | 0.00 | 3,3-dimethylpentane | 1.53 |
| butylene (C4H8) | 0.05 | 2,3-dimethylpentane | 2.74 |
| i-butane | 0.08 | 2-methylhexane | 11.87 |
| n-butane | 0.12 | 3-methylhexane | 12.07 |
| pentane | 0.10 | 3-ethylpentane | 1.74 |
| cyclopentane | 1.36 | n-heptane | 0.65 |
| i-pentane | 2.51 | methylcyclohexane | 0.46 |
| n-pentane | 1.28 | benzene | 0.96 |
| hexene | 0.70 | toluene | 0.19 |
| n-hexane | 4.82 | ethylbenzene | 0.00 |
| 2-methylpentane | 20.41 | (p + m) xylenes | 0.00 |
| 3-methylpentane | 16.34 | o-Xylene | 0.00 |
| methylcyclopentane | 8.40 | C8+ aromatics | 0.00 |

The 1 weight percent P on HZSM-5 zeolite was obtained from $NH_4$-ZSM-5 zeolite by means of an incipient wetness impregnation technique with orthophosphoric acid. More specifically, $NH_4$-ZSM-5 zeolite was intimately contacted with a solution including distilled water and orthophosphoric acid of chemical formula $H_3PO_4$, and then dried. The resulting 1 weight percent P on HZSM-5 zeolite had a surface silicon to aluminum atomic ratio of 30.

The 1 weight percent P on HZSM-5 zeolite of silicon to aluminum atomic ratio equal to 30 so obtained was utilised as a catalyst in the conversion of naphtha in a reactor at 540° C. and 1.05 bar absolute. The partial pressure of the naphtha at the inlet of the reactor was set at 0.25 bar absolute by diluting the feed naphtha with nitrogen. The fraction of feed naphtha converted was controlled by varying space time in the reactor.

Figure 1:
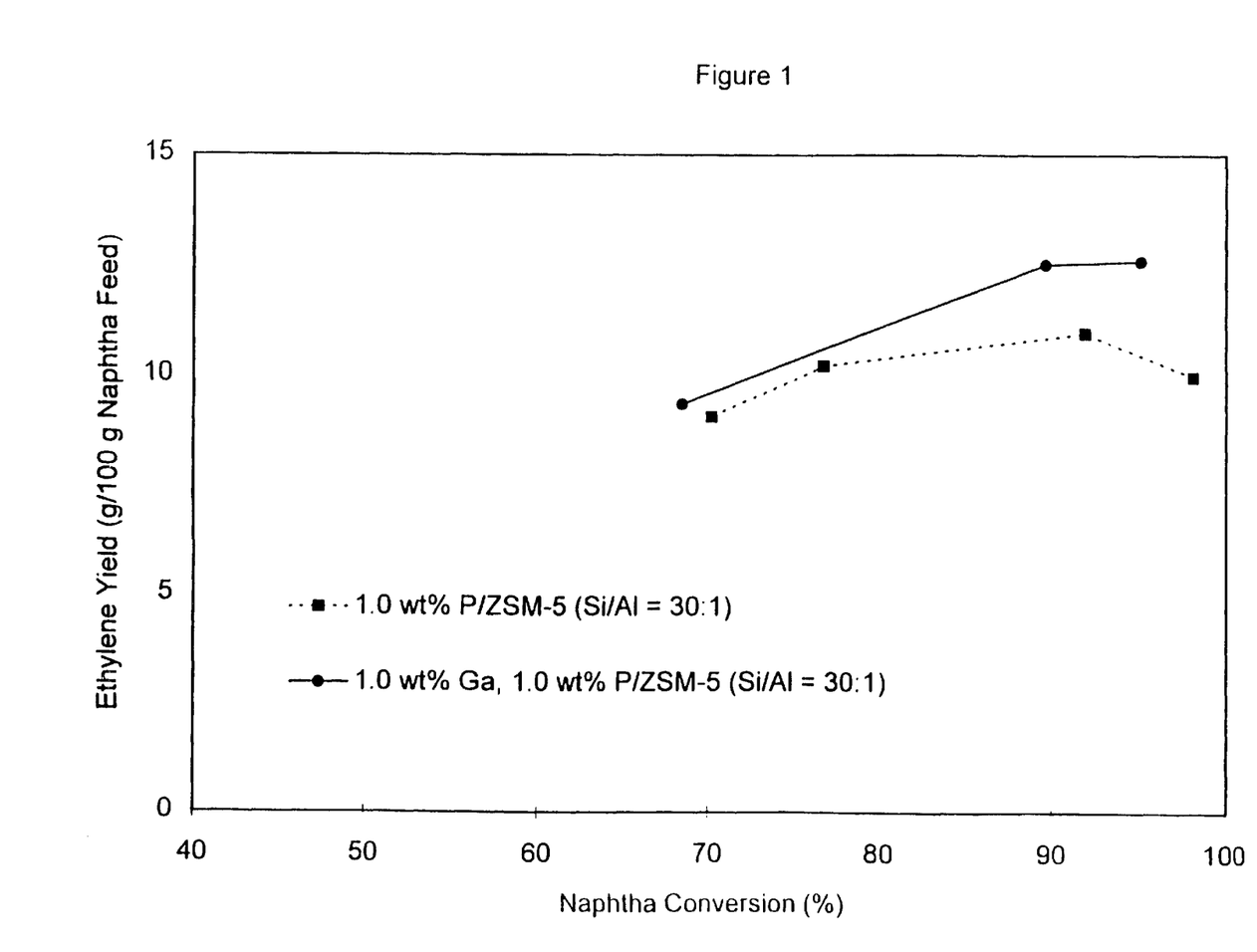
FIG. 1 is a graph showing ethylene yield as a function of naphtha conversion catalyzed by phosphorus on HZSM-5 zeolite of silicon to aluminum atomic ratio equal to 30, and by phosphorus on HZSM-5 zeolite of silicon to aluminum atomic ratio equal to 30 with gallium, respectively.

Ethylene yields observed with 1 weight percent P on HZSM-5 zeolite of silicon to aluminum atomic ratio equal to 30, represented by dark-colored square-shaped symbols, are depicted as a function of naphtha conversion in FIG. 1. Propylene yields observed with 1 weight percent P on HZSM-5, represented by dark-colored square-shaped symbols, are depicted as a function of naphtha conversion in FIG. 2. Aromatic yields observed with 1 weight percent P on HZSM-5, represented by dark-colored square-shaped symbols, are depicted as a function of naphtha conversion in FIG. 3. Additionally, the weight ratio of $C_1$ through $C_3$ paraffins produced to $C_2$ through $C_3$ olefins produced over the catalyst, represented by dark-colored square-shaped symbols, are depicted as a function of naphtha conversion in FIG. 4.

EXAMPLE 2

Conversion of Naphtha Over 1 Weight Percent Ga-1 Weight Percent P on HZSM-5 Zeolite of Silicon to Aluminum Atomic Ratio 30

An experiment was performed, and is now described in this Example 2, which demonstrates that a naphtha conversion catalyst including 1 weight percent gallium, and also including 1 weight percent P on HZSM-5 pentasil zeolite, produces a relative increase in light olefin production, while suppressing the production of aromatics and methane. In the experiment, gallium was impregnated on a sample of 1 weight percent P on HZSM-5 zeolite, which was obtained substantially as described above in Example 1. More specifically, gallium oxide ($Ga_2O_3$) was dissolved in an aqueous solution of ammonia having an alkalinity of more than 13 pH to produce a solution. The solution was brought into intimate contact with 1 weight percent P-$NH_4$-ZSM-5 zeolite. The mixture was dried and calcined in air for twelve hours at 540 degrees C. to produce 1 weight percent Ga-1 weight percent P on HZSM-5 zeolite of silicon to aluminum atomic ratio equal to 30.

Figure 2:
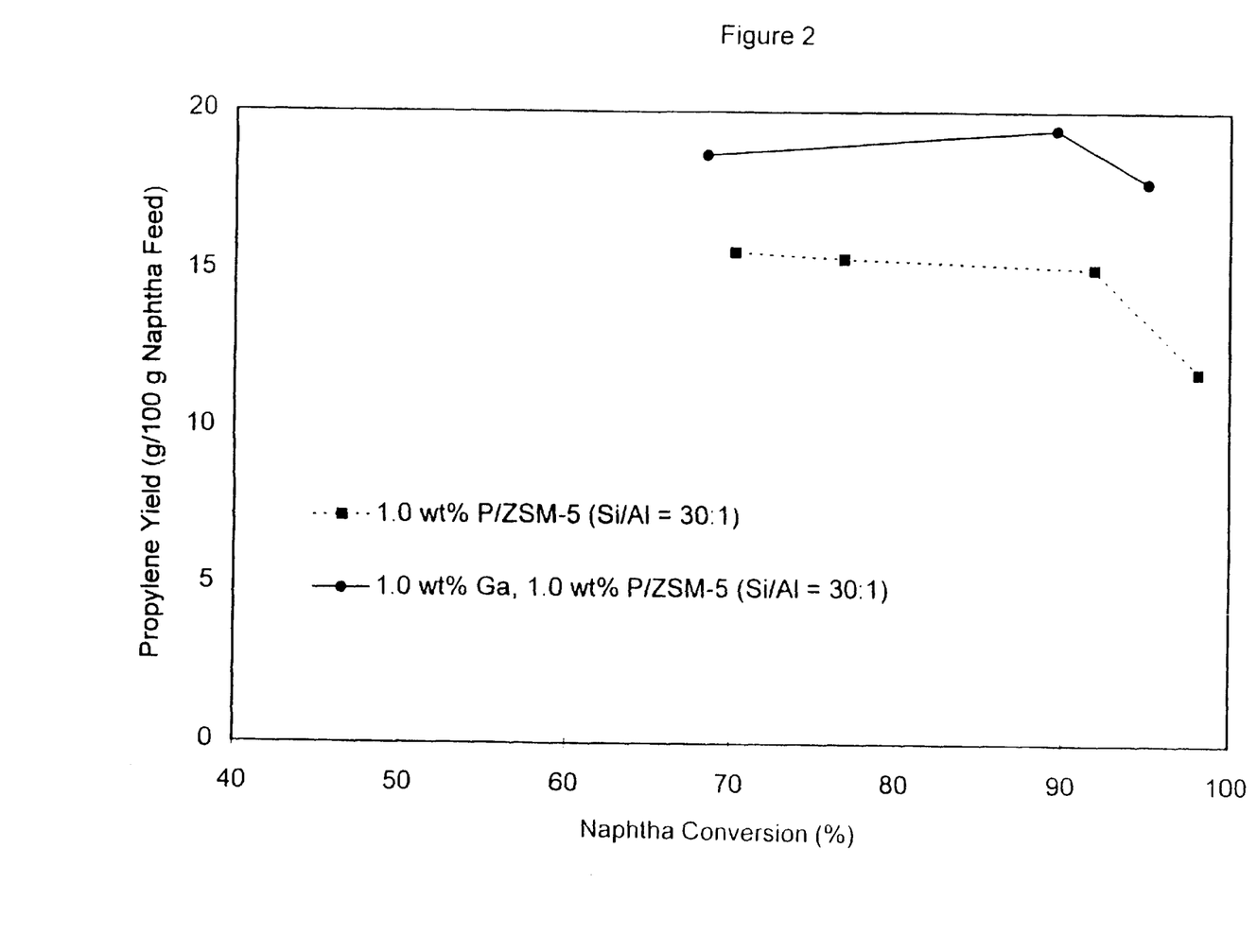
FIG. 2 is a graph showing propylene yield as a function of naphtha conversion catalyzed by phosphorus on HZSM-5 zeolite of silicon to aluminum atomic ratio equal to 30, and by phosphorus on HZSM-5 zeolite of silicon to aluminum atomic ratio equal to 30 with gallium, respectively.
Figure 3:
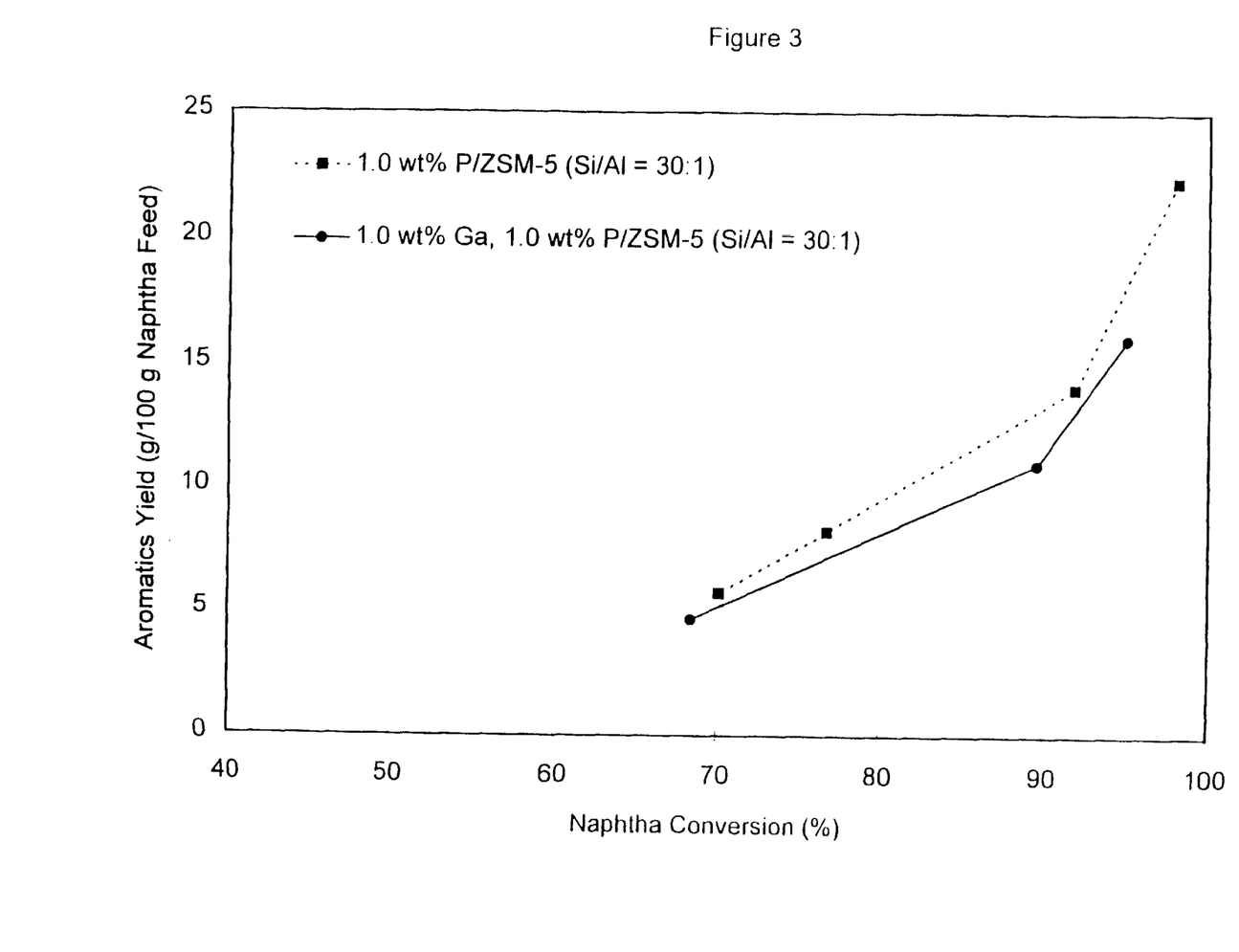
FIG. 3 is a graph showing aromatics yield as a function of naphtha conversion catalyzed by phosphorus on HZSM-5 zeolite of silicon to aluminum atomic ratio equal to 30, and by phosphorus on HZSM-5 zeolite of silicon to aluminum atomic ratio equal to 30 with gallium, respectively.

The calcined 1 weight percent Ga-1 weight percent P on HZSM-5 zeolite was subsequently utilised to convert naphtha having the composition shown above in Table 2 at substantially the same conditions which are described above in Example 1. Again, naphtha conversion was controlled by varying space time in the reactor. Ethylene, propylene and aromatics yields observed with 1 weight percent Ga-1 weight percent P on HZSM-5 of silicon to aluminum atomic ratio equal to 30, represented by dark-colored circle-shaped symbols, are depicted as a function of naphtha conversion in FIG. 1. FIG. 2 and FIG. 3, respectively. Additionally, the weight ratio of $C_1$ through $C_3$ paraffins produced to $C_2$ through $C_3$ olefins produced in the presence of the catalyst, represented by dark-colored circle-shaped symbols, are depicted as a function of naphtha conversion in FIG. 4.

Inspection of the data depicted in FIG. 1 and FIG. 2 reveals that a catalyst utilised in a process in accordance with the present invention, namely the 1 weight percent Ga-1 weight percent P on HZSM-5 zeolite of silicon to aluminum atomic ratio 30, was more selective towards ethylene and towards propylene, as compared to a previously known catalyst, which is 1 weight percent P on HZSM-5 zeolite of silicon to aluminum atomic ratio 30. Also, it can be seen from comparing these figures with FIG. 3 that, by modifying the 1 weight percent P on HZSM-5 zeolite with gallium, the production of aromatics was diminished.

Figure 4:
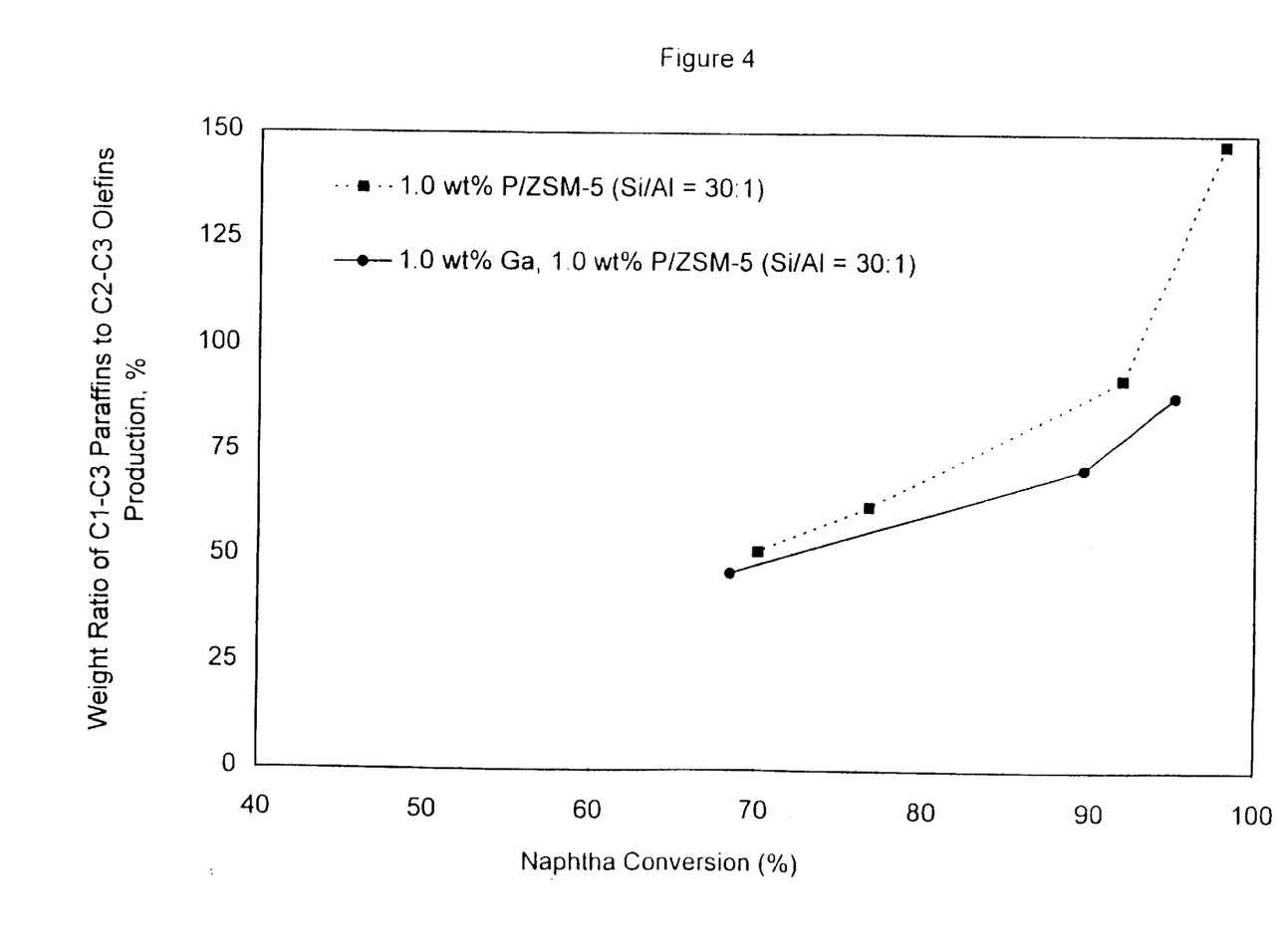
FIG. 4 is a graph showing the weight ratio of $C_1$ through $C_3$ paraffins produced to $C_2$ through $C_3$ olefins produced as a function of naphtha conversion catalyzed by phosphorus on HZSM-5 zeolite of silicon to aluminum atomic ratio equal to 30, and by phosphorus on HZSM-5 zeolite of silicon to aluminum atomic ratio equal to 30 with gallium, respectively.

Surprisingly, the data of FIG. 4 indicates that the above described advantages regarding ethylene, propylene and aromatics yields are accompanied by a relative decrease in the production of commercially less valuable light paraffins. For example, FIG. 4 indicates that the weight ratio of $C_1$ through $C_3$ paraffins produced to $C_2$ through $C_3$ olefins produced was 0.71 for the catalyst containing gallium at 89.5 percent naphtha conversion, as compared to 0.92 at 91.8 percent conversion for the previously known catalyst without gallium.

EXAMPLES 3 through 6

Gallium, Phosphorus and Silicon to Aluminum Atomic Ratio in Ga-P on HZSM-5

Employing incipient wetness procedures substantially similar to the procedures described above in Example 1 and Example 2, a series of four Ga-P on HZSM-5 zeolite catalysts were prepared from $NH_4$-ZSM-5 zeolite with silicon to aluminum atomic ratios in the range of 30 to 180 The Ga-P on HZSM-5 zeolite catalysts so prepared included gallium in the range of 0.33 to 2 weight percent and phosphorus in the range of 0.33 to 2 weight percent, based on the total weight of the catalyst. The Ga-P on HZSM-5 Zeolite catalysts were placed in a reactor at 540 degrees C. in which naphtha was converted to olefins, aromatics and paraffins.

Feed rate through the reactor was varied. Operating periods of approximately equal feed conversion by weight at space times of 175.6, 87.9, 43.9, and 22.0 grams of catalyst per mol per hour of feed rate, respectively, are reported in descending order from top to bottom in Table 3, below. During such operating periods, naphtha conversion in the range of 83.7 to 89.6 weight percent. Ethylene yield, propylene yield, butylene yield, aromatic yield and methane yield expressed in weight percent based on the total weight of the feed during such operating periods are reported below in Table 3.

TABLE 3

| Example | Ga weight percent | P weight percent | Si/Al atomic ratio | Feed Conversion | C2H4 Yield | C3H6 Yield | C4H8 Yield | Aromatic Yield | Methane Yield |
|---|---|---|---|---|---|---|---|---|---|
| 3 | 0.33 | 0.33 | 180 | 87.2 | 12.4 | 20.5 | 9.3 | 8.1 | 3.2 |
| 4 | 1 | 2 | 30 | 89.6 | 12.7 | 19.1 | 8.8 | 11.4 | 3.6 |
| 5 | 1 | 1 | 30 | 89.5 | 12.5 | 19.4 | 8.8 | 11.0 | 3.4 |
| 6 | 2 | 1 | 30 | 83.3 | 10.7 | 17.8 | 8.2 | 10.9 | 3.3 |

Inspection of the data presented in Table 3 indicates that catalysts of the present invention having silicon to aluminum atomic ratios in the range of about 30 to about 180 are desirably active and, also, that the Ga-P on HZSM-5 zeolite catalysts having lower silicon-to aluminum atomic ratios are more catalytically active for naphtha conversion. Moreover, it is apparent that Ga-P on HZSM-5 zeolite catalysts having more phosphorus tend to exhibit less activity.

The data in Table 3 indicates that increasing the weight ratio of phosphorus to gallium increases yields of etlylene, propylene and butylenes. The data in Table 3 also indicates that increasing this weight ratio inhibits aromatic and methane production. Therefore, it is preferred that the weight ratio of phosphorus to gallium is in the range of about 1:1 to about 5:1, more preferably about 2:1 to about 3:1.

EXAMPLE 7
Conversion of Naphtha Over 1 Weight Percent P on HZSM-5 Zeolite of Silicon to Aluminum Atomic Ratio 60

As another control procedure, conversion of a light naphtha was demonstrated in the presence of a previously known pentasil zeolite, 1 weight percent P on HZSM-5 zeolite having a surface of silicon to aluminum atomic ratio equal to 60. The 1 weight percent P on HZSM-5 zeolite of silicon to aluminum atomic ratio 60 was obtained from $NH_4$-ZSM-5 zeolite by substantially the same procedure as described above in Example 1, except that a relatively more concentrated orthophosphoric acid was employed for the incipient wetness impregnation. Specifically, 10 grams of $NH_4$-ZSM-5 zeolite were contacted with 5 millilitres of twice distilled water blended with 0.38 gram of orthophosphoric acid. The composition of the naphtha feed employed in this Example, and the naphtha conversion process utilised in this Example, are substantially the same as described above in Example 1.

Figure 5:
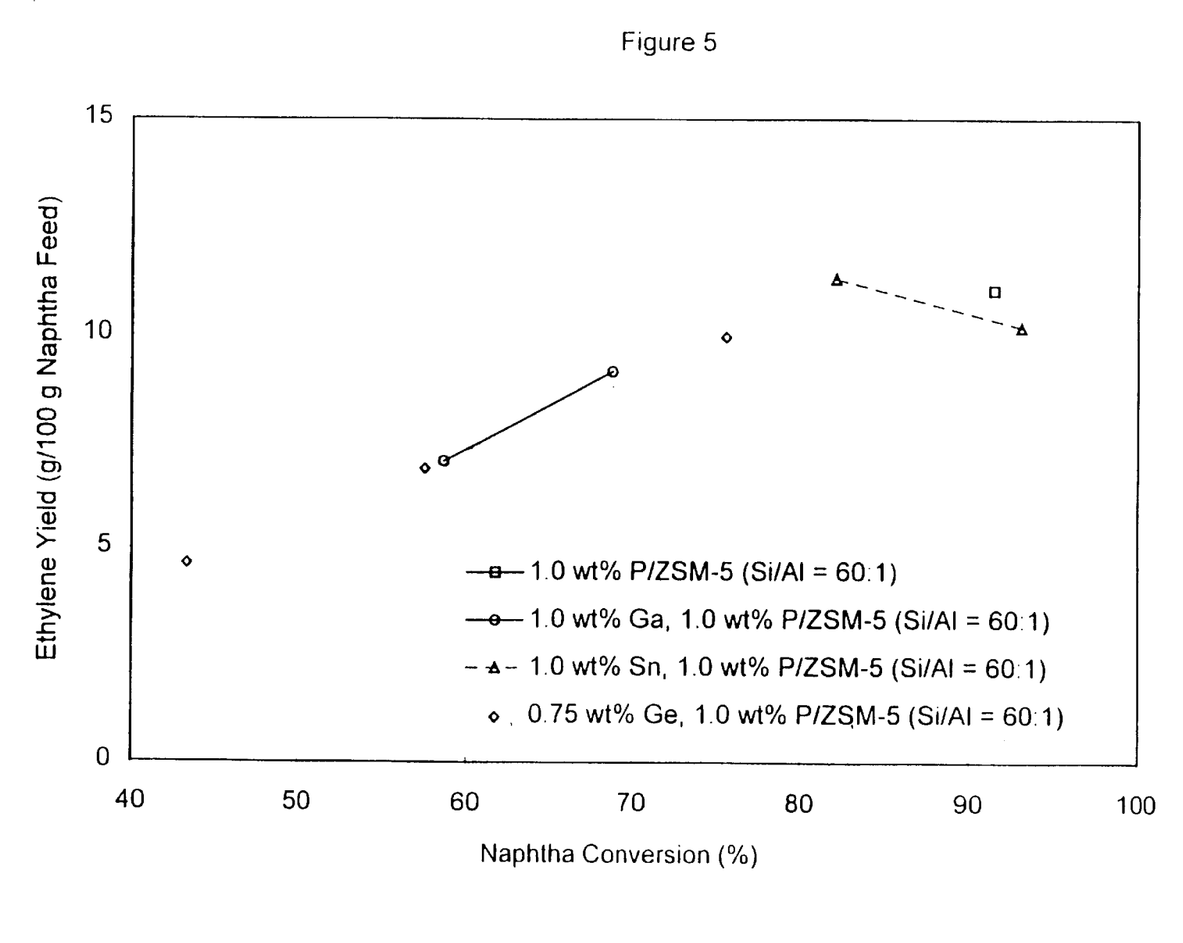
FIG. 5 is a graph showing ethylene yield as a function of naphtha conversion catalyzed by phosphorus on HZSM-5 zeolite of silicon to aluminum atomic ratio equal to 60, and by phosphorus on HZSM-5 zeolite of silicon to aluminum atomic ratio equal to 60 with gallium, germanium or tin, respectively.
Figure 6:
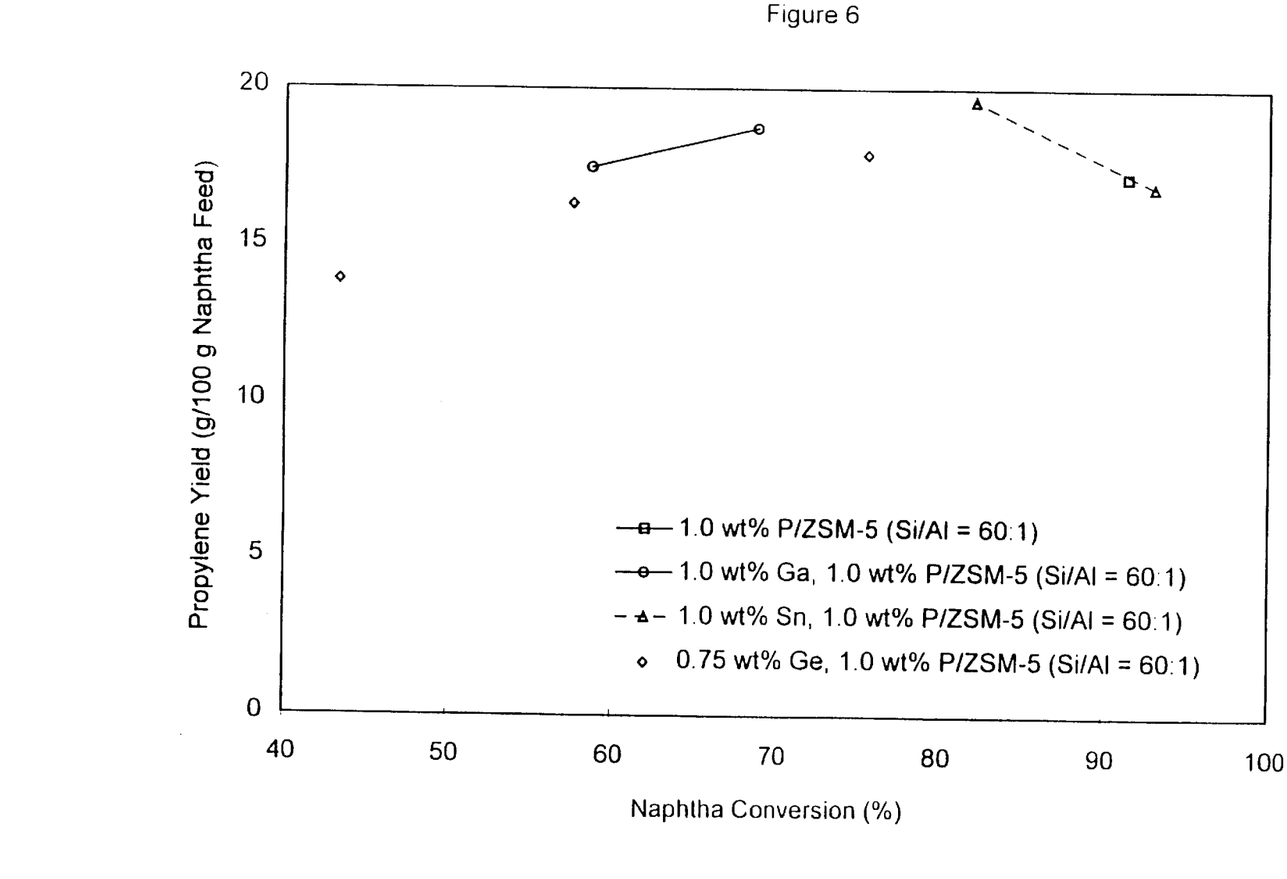
FIG. 6 is a graph showing propylene yield as a function of naphtha conversion catalyzed by phosphorus on HZSM-5 zeolite of silicon to aluminum atomic ratio equal to 60, and by phosphorus on HZSM-5 zeolite of silicon to aluminum atomic ratio equal to 60 with gallium, germanium or tin, respectively.
Figure 7:
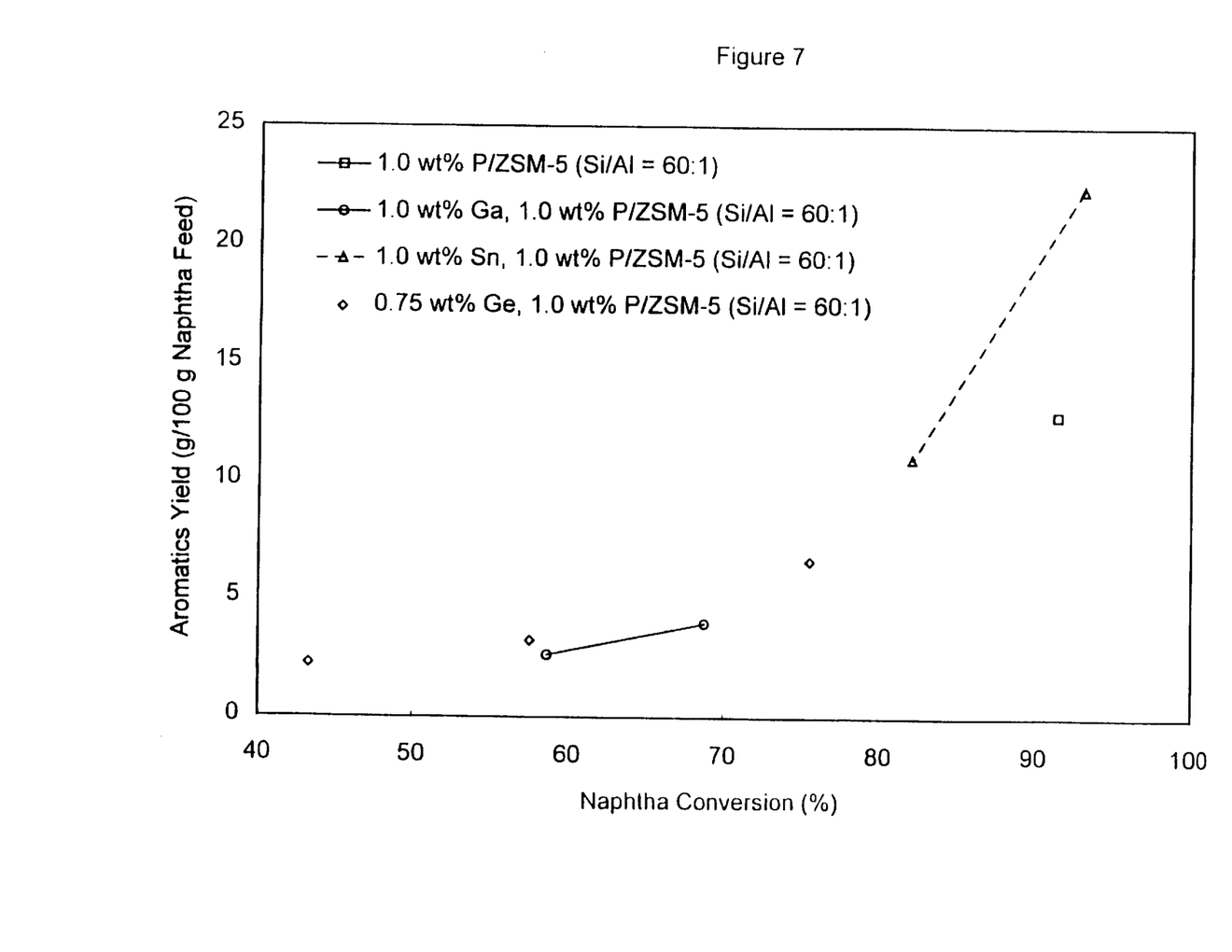
FIG. 7 is a graph showing aromatics yield as a function of naphtha conversion catalyzed by phosphorus on HZSM-5 zeolite of silicon to aluminum atomic ratio equal to 60, and by phosphorus on HZSM-5 zeolite of silicon to aluminum atomic ratio equal to 60 with gallium, germanium or tin, respectively.
Figure 8:
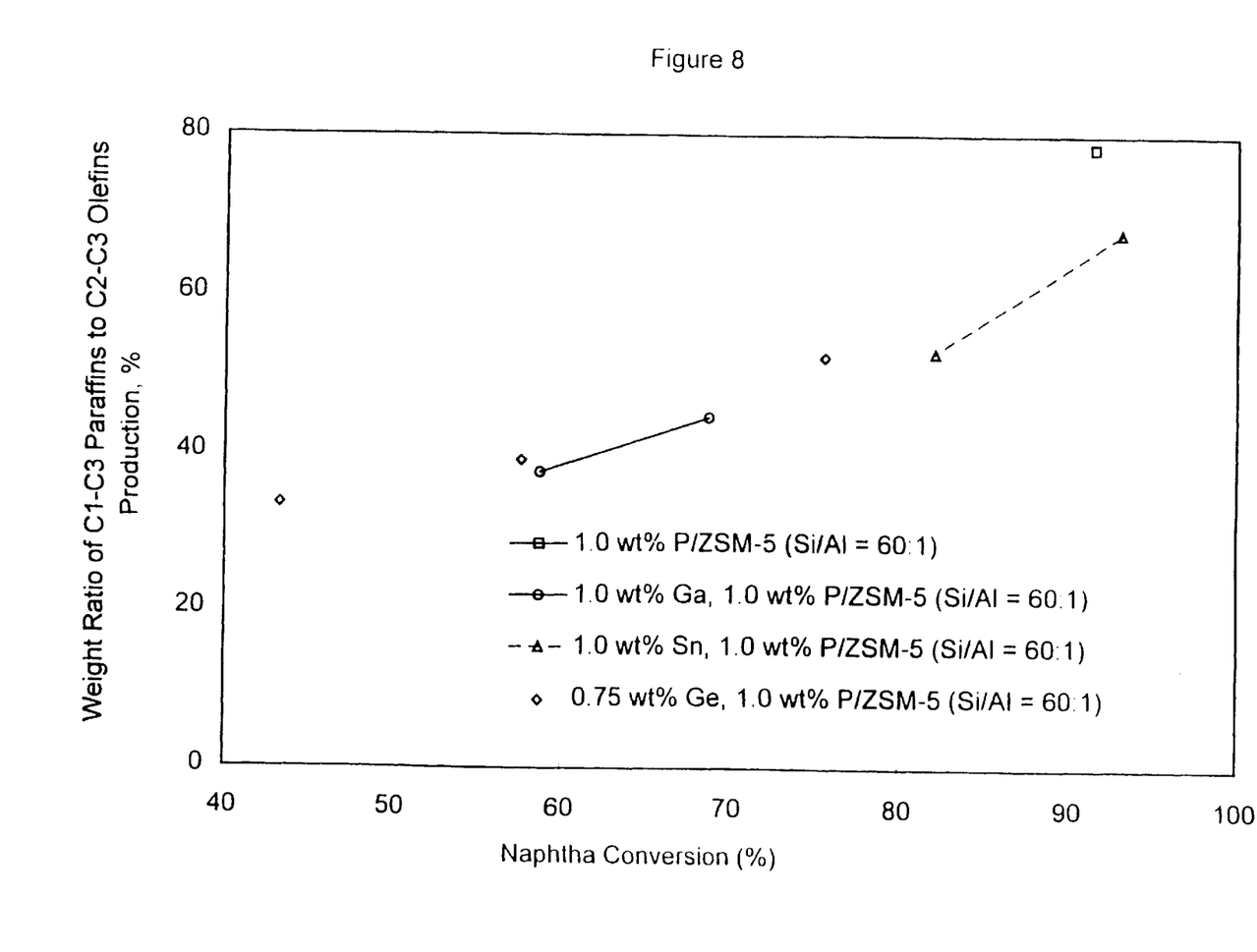
FIG. 8 is a graph showing the weight ratio of $C_1$ through $C_3$ paraffins produced to $C_2$ through $C_3$ olefins produced as a function of naphtha conversion catalyzed by phosphorus on HZSM-5 zeolite of silicon to aluminum atomic ratio equal to 60, and by phosphorus on HZSM-5 zeolite of silicon to aluminum atomic ratio equal to 60 with gallium, germanium or tin, respectively.

Ethylene, propylene and aromatics yields observed with 1 weight percent Ga-1 weight percent P on HZSM-5 of silicon to aluminum atomic ratio equal to 60, represented by light-colored square-shaped symbols, are depicted as a function of naphtha conversion in FIG. 5, FIG. 6 and FIG. 7, respectively. Additionally, the weight ratio of $C_2$ through $C_3$ paraffins produced to $C_2$ through $C_3$ olefins produced in the presence of the catalyst, represented by light-colored square-shaped symbols, are depicted as a function of naphtha conversion in FIG. 8.

EXAMPLE 8

Conversion of Naphtha Over 1 Weight Percent Ga-1 Weight Percent P on HZSM-5 Zeolite of Silicon to Aluminum Atomic Ratio 60

A catalyst consisting of 1 weight percent Ga-1 weight percent P on HZSM-5 zeolite of silicon to aluminum atomic ratio equal to 60 was subsequently prepared by impregnating gallium onto a 1 weight percent P on HZSM-5 zeolite of silicon to aluminum atomic ratio equal to 60, which had been prepared by the method described above in Example 7. This catalyst was used to convert naphtha having the composition shown above in Table 2 at substantially the same conditions described above in Example 1. Again, naphtha conversion was controlled by varying space time in the reactor.

Ethylene, propylene and aromatics yields observed with 1 weight percent Ga-1 weight percent P on HZSM-5 of silicon to aluminum atomic ratio equal to 60, represented by light-colored circle-shaped symbols, are depicted as a function of naphtha conversion in FIG. 5, FIG. 6 and FIG. 7, respectively. Additionally, the weight ratio of $C_1$ through $C_3$ paraffins produced to $C_2$ through $C_3$ olefins produced over the catalyst, represented by light-colored circle-shaped symbols, are depicted as a function of naphtha conversion in FIG. 8.

EXAMPLE 9

Conversion of Naphtha Over 1 Weight Percent Sn-1 Weight Percent P on HZSM-5 Zeolite of Silicon to Aluminum Atomic Ratio 60

An incipient wetness impregnation procedure was performed which is substantially similar to the procedure described above in Example 7, except that tin chloride ($SnCl_2$) was dissolved in acetone to produce an impregnating solution, rather than gallium oxide ($Ga_2O_3$) being dissolved in an aqueous solution of ammonia. An appropriate amount of the tin chloride-acetone solution was brought into intimate contact with 1 weight percent P-$NH_4$-ZSM-5 zeolite having a silicon to aluminum atomic ratio of 60. The resulting mixture was dried and reduced in hydrogen at elevated temperature to produce 1 weight percent Sn-1 weight percent P on HZSM-5 zeolite.

The 1 weight percent Sn-1 weight percent P on HZSM-5 zeolite was utilised as a catalyst to promote the conversion of naphtha having the composition set forth above in Table 2, in a reactor maintained at substantially the conditions described above in Example 1. Ethylene, propylene and aromatics yields observed with 1 weight percent Ga-1 weight percent P on HZSM-5 of silicon to aluminum atomic ratio equal to 60, represented by light-colored triangle-shaped symbols, are depicted as a function of naphtha conversion in FIG. 5, FIG. 6 and FIG. 7, respectively. Additionally, the weight ratio of $C_1$ through $C_3$ paraffins produced to $C_2$ through $C_3$ olefins produced over the catalyst, represented by light-colored triangle-shaped symbols, are depicted as a function of naphtha conversion in FIG. 8.

Inspection of the data depicted in FIG. 5 and FIG. 6 reveals that the 1 weight percent Sn-1 weight percent P on HZSM-5 zeolite of silicon to aluminum atomic ratio equal to 60, which zeolite is a catalyst in accordance with the present invention, was about as selective towards ethylene and towards propylene, as compared to the previously known 1 weight percent P on HZSM-5 zeolite of silicon to aluminum atomic ratio equal to 60. It can be seen from these figures and from FIG. 7 that, by modifying the 1 weight percent P on HZSM-5 zeolite with tin, the production of aromatics was increased. However, inspection of FIG. 8 indicates that the tin containing zeolite produced much less methane, ethane and propane, as compared to the previously known catalyst.

EXAMPLE 10

Conversion of Naphtha Over 0.75 Weight Percent Ge-1 Weight Percent P on HZSM-5 Zeolite of Silicon to Aluminum Atomic Ratio 60

An incipient wetness impregnation procedure, similar to the procedure described above in Example 4, was performed in which germanium was impregnated on 1 weight percent P on HZSM-5 having a silicon to aluminum atomic ratio of 60, calcined and reduced to produce 0.75 weight percent Ge-1 weight percent P on HZSM-5 zeolite of silicon to aluminum atomic ratio 60. The 0.75 weight percent Ge-1 weight percent P on HZSM-5 zeolite was utilised as a catalyst to promote the conversion of naphtha having the composition set forth above in Table 2, in a reactor maintained at substantially the conditions described above in Example 1.

Ethylene, propylene and aromatics yields observed with 0.75 weight percent Ge-1 weight percent P on HZSM-5 of silicon to aluminum atomic ratio equal to 60, represented by light-colored diamond-shaped symbols, are depicted as a function of naphtha conversion in FIG. 5, FIG. 6 and FIG. 7, respectively. Additionally, the weight ratio of $C_1$ through $C_3$ paraffins produced to $C_2$ through $C_3$ olefins produced in the presence of the catalyst, represented by light-colored diamond-shaped symbols, is depicted as a function of naphtha conversion in FIG. 8.

Inspection of the data depicted in FIG. 5 and FIG. 6 reveals that the 0.75 weight percent Ge-1 weight percent P on HZSM-5 zeolite of silicon to aluminum atomic ratio equal to 60, which zeolite is a catalyst in accordance with the present invention, was about as selective towards ethylene and towards propylene, as was the 1 weight percent Ga-1 weight percent P on HZSM-5 zeolite of silicon to aluminum atomic ratio equal to 60, which was described above in Example 5. It can be seen from these figures and from FIG. 7 that modifying the 1 weight percent P on HZSM-5 zeolite with 0.75 weight percent germanium provided a catalyst which produced aromatics in about the same proportion as did the 1 weight percent Ga-1 weight percent P on HZSM-5 zeolite of Example 5. Moreover, inspection of FIG. 8 indicates that the 0.75 weight percent Ge-1 weight percent P on HZSM-5 zeolite of silicon to aluminum atomic ratio 60 described in this Example, produced about the same amounts of methane, ethane and propane, as did the 1 weight percent Ga-1 weight percent P on HZSM-5 zeolite of silicon to aluminum atomic ratio equal to 60 described in Example 5.

Based on the data illustrated I FIG. 1 through FIG. 8, it may be concluded that the Ga-P on HZSM-5 zeolite, the Sn-P on HZSM-5 zeolite and the 0.75 Ge-P on HZSM-5 zeolite are all effective catalysts for ethylene and propylene manufacturing by naphtha conversion. Moreover, the Sn-P on HZSM-5 zeolite is especially appropriate when low selectivities toward light paraffins are desired. When aromatics are not a primarily desired product, as in propylene manufacturing, the Ga-P on HZSM-5 zeolite is recommended because the zeolite suppresses aromatization while providing a relatively high yield of ethylene and propylene.

The above examples and hypotheses are intended to better communicate the invention. These examples and hypotheses do not limit the scope of the invention which is defined by the claims presented below.

That which is claimed is:

1. A process for producing at least one light olefin and relatively less aromatic products, comprising: contacting at a temperature of 400° C. to 650° C. and a pressure of 1 to 3 atmospheres, a feedstock comprising a volatile hydrocarbon mixture which is liquid at room temperature and pressure in a reactor with a catalyst comprising a ZSM-5 zeolite catalyst which contains 0.1 to 10 weight percent phosphorus and 0.1 to 10 weight percent of a promoter metal which is gallium, based on the total weight of the catalyst, and the weight ratio of phosphorus to gallium is in the range of 1:1 to 5:1, under effective reaction conditions to produce at least one olefin having two to three carbon atoms per molecule.

2. The process of claim 1 wherein the feedstock enters the reactor with a heat conducting diluent composed of nitrogen, steam and/or a relatively refractory hydrocarbon, and wherein the molar ratio of the diluent to feedstock is in a range of 9 to 0.1.

3. The process of claim 1 wherein the feedstock enters the reactor with a co-feed composed substantially of propane, and wherein the molar ratio of co-feed propane to feedstock is about 6 to about 1.

4. The process of claim 1 wherein the light olefin is propylene.

5. The process of claim 1 wherein the catalyst has a silicon to aluminum atomic ratio in the range of 10 to 400, and the volatile hydrocarbon mixture exhibits an atmospheric volumetric average boiling point in the range of negative 22° C. to 466° C.

6. A process for producing light olefins and relatively less aromatic products, comprising: contacting a naphtha including a paraffin having four to eleven carbon atoms per molecule in a reactor at a temperature of 400 to 650 degrees C. and a pressure of one to two atmospheres with a ZSM-5 zeolite catalyst having a silicon to aluminum atomic ratio of 10o to 400 and containing 0.1 to 10 weight percent phosphorus and 0.1 to 10 weight percent of a promoter metal which is gallium, and the weight ratio of phosphorus to gallium is in the range of 1:1 to 5:1, to produce light olefins having two to three carbon atoms per molecule.

7. The process of claim 6 wherein the naphtha exhibits an atmospheric volumetric average boiling point in the range of negative 1° C. to 204° C., and the naphtha is passed into the reactor with a diluent selected from the group consisting of steam, nitrogen, methane, ethane and mixtures thereof, and wherein the molar ratio of the diluent to naphtha is maintained in a range of 9 to 0.1.

8. The process of claim 6 wherein the naphtha exhibits an atmospheric volumetric average boiling point in the range of negative 1° C. to 204° C., and the naphtha is passed into the reactor together with a co-feed composed substantially of propane, and wherein the molar ratio of co-feed propane passed into the reactor to the naphtha passed into the reactor is in a range of 6 to 1.

* * * * *

UNITED STATES PATENT AND TRADEMARK OFFICE
CERTIFICATE OF CORRECTION

PATENT NO. : 6,548,725 B2
DATED : April 15, 2003
INVENTOR(S) : Gilbert Fernand Alphonse Froment et al.

It is certified that error appears in the above-identified patent and that said Letters Patent is hereby corrected as shown below:

Column 6,
Lines 31-32, ", most preferably about 0.75 to about weight percent" should read
-- , most preferably about 0.75 to about 2 weight percent --

Column 10,
Line 20, "Additionally, the weight ratio of $\mathbf{C_2}$ through $C_3$ paraffins" should read
-- Additionally, the weight ratio of $\mathbf{C_1}$ through $C_3$ paraffins --

Column 13,
Lines 11-12, "atomic ratio of 10o to 400 and" should read -- atomic ratio of 10 to 400 and --

Signed and Sealed this

Ninth Day of September, 2003

JAMES E. ROGAN
*Director of the United States Patent and Trademark Office*